United States Patent
Tashiro et al.

(10) Patent No.: US 9,030,544 B2
(45) Date of Patent: May 12, 2015

(54) WIRELESS VIDEO TRANSMISSION SYSTEM AND TRANSMISSION DEVICE

(71) Applicant: Olympus Medical Systems Corp., Tokyo (JP)

(72) Inventors: Hideki Tashiro, Tokyo (JP); Koichi Tashiro, Sagamihara (JP); Junichi Tashiro, Tokyo (JP); Masashi Umemura, Tokyo (JP); Kyuma Tanida, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/837,807

(22) Filed: Mar. 15, 2013

(65) Prior Publication Data

US 2013/0265402 A1 Oct. 10, 2013

Related U.S. Application Data

(63) Continuation of application No. PCT/JP2012/063058, filed on May 22, 2012.

(30) Foreign Application Priority Data

Sep. 9, 2011 (JP) .................................. 2011-197387

(51) Int. Cl.
*A61B 1/00* (2006.01)
*H04N 7/18* (2006.01)

(52) U.S. Cl.
CPC ......... *A61B 1/00016* (2013.01); *A61B 1/00045* (2013.01); *A61B 1/00059* (2013.01); *H04N 7/185* (2013.01)

(58) Field of Classification Search
CPC ....................................................... A61B 1/00
See application file for complete search history.

(56) References Cited

U.S. PATENT DOCUMENTS

| | | | | |
|---|---|---|---|---|
| 2003/0093503 | A1* | 5/2003 | Yamaki et al. | ................ 709/220 |
| 2012/0200688 | A1 | 8/2012 | Endo et al. | |

FOREIGN PATENT DOCUMENTS

| | | |
|---|---|---|
| EP | 2 360 955 A1 | 8/2011 |
| EP | 2 445 210 A1 | 4/2012 |
| EP | 2 493 193 A1 | 8/2012 |
| JP | A-2001-104331 | 4/2001 |

(Continued)

OTHER PUBLICATIONS

International Search Report issued in International Patent Application No. PCT/JP2012/063058 dated Aug. 28, 2012.

(Continued)

*Primary Examiner* — Sath V Perungavoor
*Assistant Examiner* — Jeffery Williams
(74) *Attorney, Agent, or Firm* — Oliff PLC

(57) ABSTRACT

In a transmission device used in a wireless video transmission system in which a medical image is transmitted and received by radio communication, a transmission unit is capable of performing radio communication with a plurality of receiving devices connected to a plurality of display apparatuses. A control unit acquires an identifier for identifying a receiving device connected to a selected single display apparatus when an instruction is received to select one display apparatus on which the medical image is to be displayed from among the display apparatuses, and controls the transmission unit such that the identifier will be used when the medical image is transmitted.

6 Claims, 16 Drawing Sheets

(56) References Cited

FOREIGN PATENT DOCUMENTS

| JP | A-2002-125219 | 4/2002 |
|---|---|---|
| JP | A-2005-342400 | 12/2005 |
| JP | A-2007-307298 | 11/2007 |
| JP | A-2008-99875 | 5/2008 |
| JP | A-2010-288186 | 12/2010 |
| WO | WO 2010/146760 A1 | 12/2010 |
| WO | WO 2011/049163 A1 | 4/2011 |
| WO | WO 2011049163 A1 * | 4/2011 |

OTHER PUBLICATIONS

Written Opinion of the International Searching Authority issued in International Patent Application No. PCT/JP2012/063058 dated Aug. 28, 2012 (w/translation).
Feb. 5, 2015 Extended European Search Report issued in European Patent Application No. 12830139.7.
"Address Resolution Protocol" retrieved Jan. 28, 2015, http://en.wikipedia.org/w/index.php?title=Address_Resolution_Protocol&oldid=449055192.

* cited by examiner

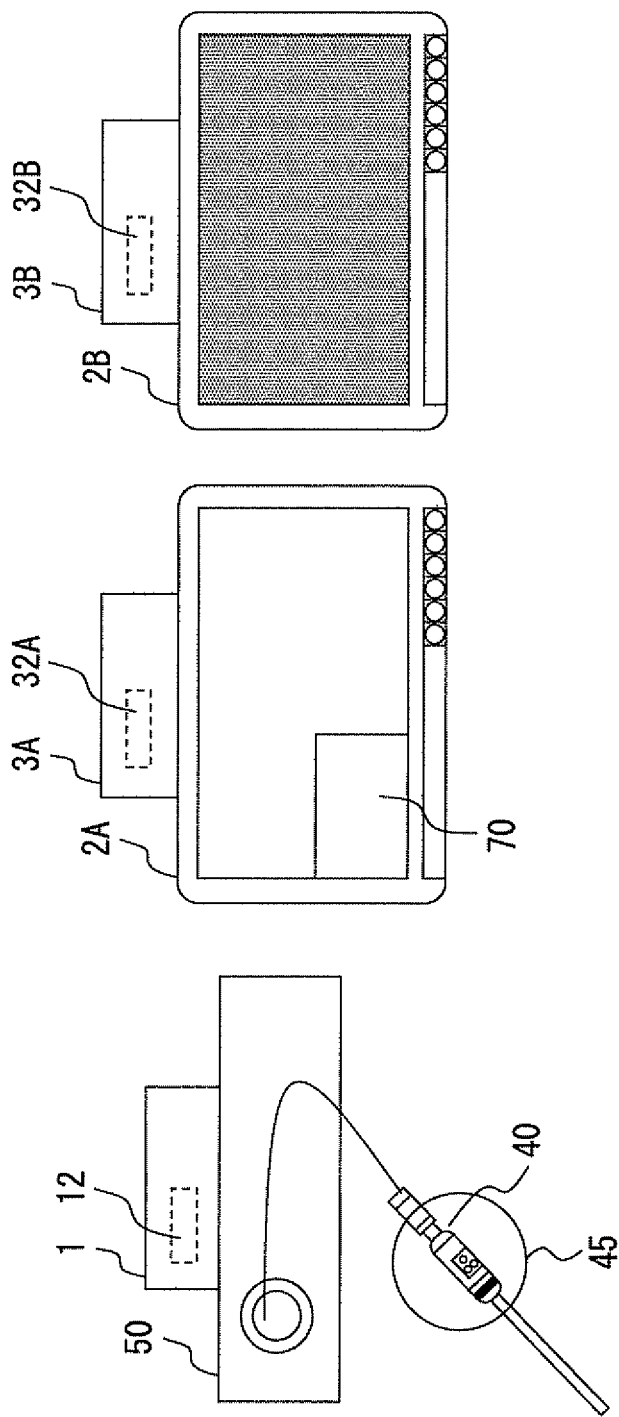

DO YOU WANT TO DISPLAY VIDEO ON THIS MONITOR?
[YES]   ···BUTTON 1
[NO]    ···BUTTON 2

FIG. 9

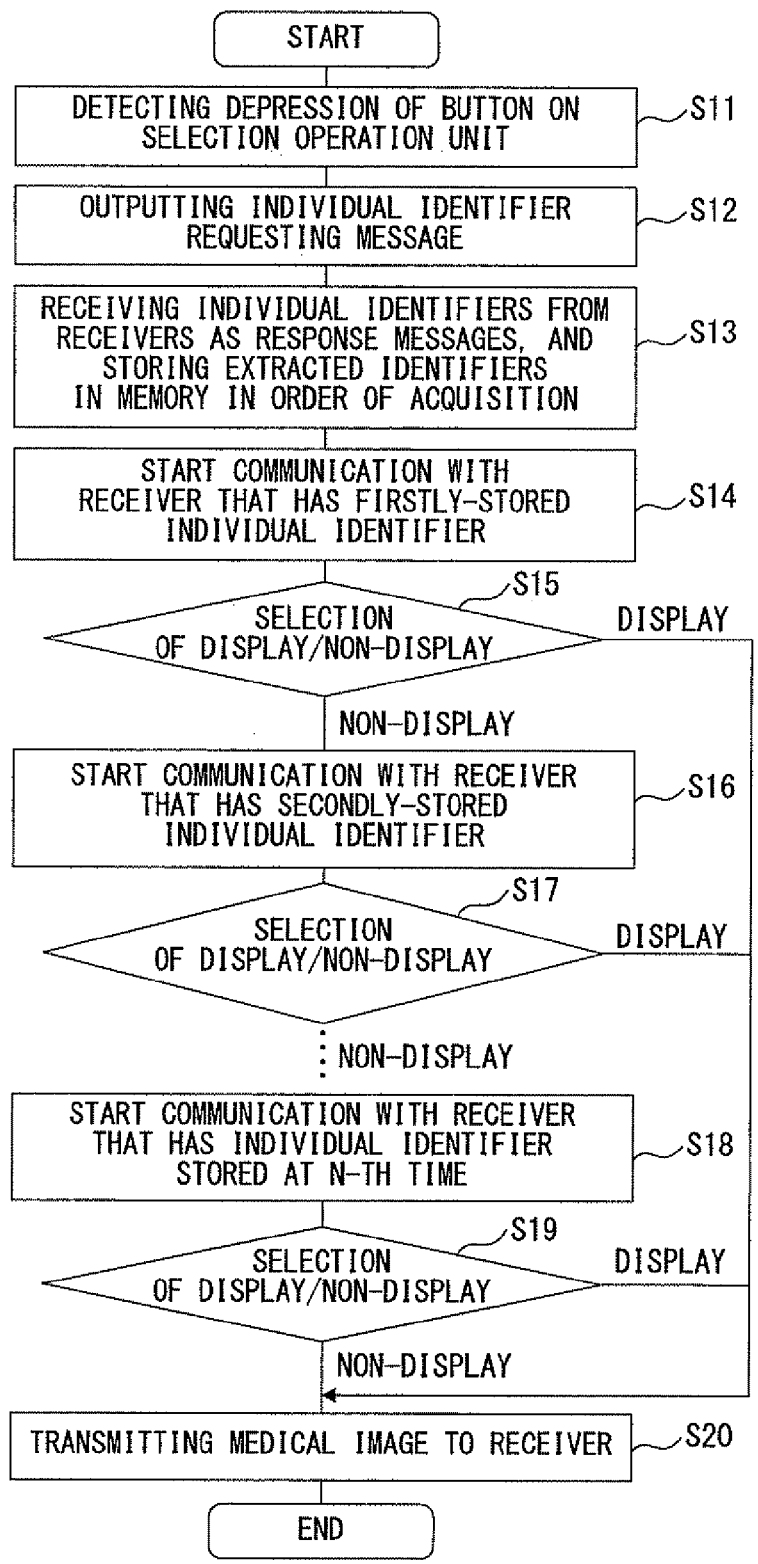
F I G. 1 2

WIRELESS VIDEO TRANSMISSION SYSTEM AND TRANSMISSION DEVICE

CROSS-REFERENCE TO RELATED APPLICATIONS

This application is based upon and claims the benefit of priority of the prior Japanese Patent Application No. 2011-197387, filed Sep. 9, 2011, the entire contents of which are incorporated herein by reference.

This is a Continuation Application of PCT Application No. PCT/JP2012/063058, filed May 22, 2012, which was not published under PCT Article 21(2) in English.

FIELD

The present invention relates to a video transmission system and a transmission device in which a medical image is transmitted from the transmission device to a receiving device. In particular, the present invention relates to a video transmission system and a transmission device in which a medical image is transmitted by radio communication.

BACKGROUND

Conventionally, a method is generally used where medical images such as endoscopic images are displayed on a monitor via video cables and a practitioner performs endoscopic surgery while viewing the image on the monitor.

In endoscopic surgery, it is usually the situation that, when the position where a practitioner stands changes depending on the medical case or the manipulation progresses, the optimal position of a monitor on which medical images such as endoscopic Images are displayed also changes accordingly. As a way of iealing with changes in an optimal position of a monitor, the number of operating rooms where two or more monitors are installed has been increasing.

Conventionally, when an endoscopic image is to be displayed on a monitor that a practitioner wishes to display it on in an operating room where two or more monitors are installed, generally a person other than the practitioner, for example, a surrounding nurse or the like being instructed by the practitioner, switches monitors. This is because the practitioner is unable to touch equipment in a non-sterilized area (unclean area) while he/she remains in a sterilized area of the operating room.

When monitors are to be switched, a surrounding nurse for example unplugs the video cable from a monitor that is difficult for the practitioner to see, and plugs the video cable into a monitor at a more convenient position to see. In this case, it is necessary to unplug and plug back in a video cable, and this is troublesome.

Alternatively, the same number of video cables as the number of monitors may be connected in advance, and a surrounding nurse performs an input selecting operation or the like of the monitors as instructed by a practitioner.

For example, Japanese Laid-open Patent Publication No. 2002-125219 discloses a technique in which observation images of an endoscope are displayed on two or more, monitors in a synchronized manner.

Moreover, Japanese Laid-open Patent Publication No. 2005-342400 discloses a technique in which a radio transmission circuit provided in a processor transmits by radio the subject images acquired by an image pickup device to an external monitor as a video signal.

SUMMARY

It is desired that the video of medical images or the like be wirelessly displayed on a monitor that a practitioner wishes to display it on or the like from among two or more monitors.

A transmission device according to one aspect of the present invention is a transmission device used in a wireless video transmission system in which a medical image is transmitted and received by radio communication, and the transmission device includes: a transmission unit capable of performing radio communication with a plurality of receiving devices connected to a plurality of display apparatuses; a control unit configured to acquire an identifier for identifying a receiving device connected to a selected single display apparatus when an instruction is received to select one display apparatus on which the medical image is to be displayed from among the display apparatuses, and configured to control the transmission unit such that the identifier will be used when the medical image is transmitted; and a generating unit configured to generate an acquisition request requesting an identifier of the receiving device connected to the display apparatus, wherein the control unit controls the transmission unit to transmit the acquisition request by using a specified channel set to the receiving devices in common, and controls the transmission unit such that an identifier indicating the receiving device connected to the selected display apparatus from among identifiers included in responses given to the acquisition request will be set to a destination of transmission and the medical image will be transmitted, and in a control process for the transmission unit, the control unit acquires a first identifier from a firstly received first response from among the responses received from the receiving devices connected to the display apparatuses, and sets the first identifier to a destination of transmission and controls the transmission unit so as to start performing radio communication with the receiving device connected to the display apparatus, controls the transmission unit so as to start transmitting the medical image to the receiving device that is performing communication when an instruction is received to select the display apparatus to which the receiving device that is performing communication is connected, and acquires a second identifier from a second response received after the first response and sets the second identifier to a destination of transmission to control the transmission unit so as to start performing radio communication with the receiving device when an instruction is received not to select the display apparatus to which the receiving device that is performing communication is connected, and repeats the above processes until an instruction to select the receiving device that is performing communication is received.

A transmission device according to another aspect of the present invention is a transmission device used in a wireless video transmission system in which a medical image is transmitted and received by radio communication, and the transmission device includes: a transmission unit capable of performing radio communication with a plurality of receiving devices connected to a plurality of display apparatuses; a control unit configured to acquire an identifier for identifying a receiving device connected to a selected single display apparatus when an instruction is received to select one display apparatus on which the medical image is to be displayed from among the display apparatuses, and configured to control the transmission unit such that the identifier will be used when the medical image is transmitted; and a storage unit configured to store identifiers indicating the receiving devices connected to the display apparatuses, wherein the control unit reads from the storage unit, an identifier indicating the receiving device connected to the selected display apparatus, and controls the transmission unit to set the read identifier to a destination of transmission and to perform transmission of the medical image.

A wireless video transmission system according to another aspect, of the present invention is a wireless video transmission system including a transmission device and a receiving device that transmit and receive a medical image by radio communication, and the transmission device includes: a transmission unit capable of performing radio communication with a plurality of receiving devices connected to a plurality of display apparatuses; a control unit configured to acquire an identifier for identifying a receiving device connected to a selected single display apparatus when an instruction is received to select one display apparatus on which the medical image is to foe displayed from among the display apparatuses, and configured to control the transmission unit such that the identifier will be used when the medical image is transmitted; and a generating unit configured to generate an acquisition request requesting an identifier of the receiving device connected to the display apparatus, and the receiving device includes a receiver configured to receive the medical image transmitted by using the identifier, wherein the control unit of the transmission device controls the transmission unit to transmit the acquisition request by using a specified channel set to the receiving devices in common, and controls the transmission unit such that an identifier indicating the receiving device connected to the selected display apparatus from among identifiers included in responses given to the acquisition request will be set to a destination of transmission and the medical image will be transmitted, and in a control process for the transmission unit, the control unit acquires a first identifier from a firstly received first response from among the responses received from the receiving devices connected to the display apparatuses, and sets the first identifier to a destination of transmission and controls the transmission unit so as to start performing radio communication with the receiving device connected to the display apparatus, controls the transmission unit so as to start transmitting the medical image to the receiving device that is performing communication when an instruction is received to select the display apparatus to which the receiving device that is performing communication is connected, and acquires a second identifier from a second response received after the first response and sets the second identifier to a destination of transmission to control the transmission unit so as to start performing radio communication with the receiving device when an instruction is received not to select the display apparatus to which the receiving device that is performing communication is connected, and repeats the above processes until an instruction to select the receiving device that, is performing communication is received.

A wireless video transmission system according to another aspect of the present invention is a wireless video transmission system including: a video signal transmission unit for transmitting a video signal by radio, which is used to display an observation image; identification signal transmission unit for selectively transmitting a first identification signal and a second identification signal by radio, which are used to specify a monitor on which the video signal is to be displayed; a transmission device having the video signal transmission unit and the identification signal transmission unit; a first identification signal recognition unit, configured to recognize a first, identification signal transmitted from the transmission device; a first video signal receiving unit configured to receive a video signal from the transmission device according to a result of recognition by the first identification signal recognition unit; a first display unit capable of displaying the video signal received by the first video signal receiving unit; a first, monitor having the first identification signal recognition unit, and the first video signal receiving unit, and the first display unit; a second identification signal recognition unit configured to recognize a second identification signal transmitted from the transmission device; a second video signal receiving unit configured to receive a video signal from the transmission device according to a result of recognition by the second identification signal recognition unit; a second display unit capable of displaying the video signal received by the second video signal receiving unit; and a second monitor having the second identification signal recognition unit and the second video signal receiving unit, and the second display unit, wherein the transmission device controls the identification signal transmission unit to transmit the acquisition request by using a specified channel set to the first and second monitors in common, and controls the video signal transmission unit such that an identifier indicating the selected receiving unit of the first or second monitor from among identifiers included in responses given to the acquisition request will be set to a destination of transmission and the medical image will be transmitted, and in a control process for the identification signal transmission unit and the video signal transmission unit, the transmission device acquires a first identifier from a firstly received first response from among the responses received from the first, and second monitors, and sets the first identifier to a destination of transmission and controls the video signal transmission unit so as to start performing radio communication with the first or second monitor, controls the video signal transmission unit so as to start transmitting the medical image to the first or second monitor that is performing communication when an instruction is received to select the first or second monitor that is performing communication, and acquires a second identifier from a second response received after the first response and sets the second identifier to a destination of transmission to control the video signal transmission unit so as to start performing radio communication with the first or second monitor when an instruction is received not to select the first or second monitor that is performing communication, and repeats the above processes until an instruction to select the first or second monitor that is performing communication is received.

BRIEF DESCRIPTION OF DRAWINGS

The present invention will be more apparent from the following detailed description when the accompanying drawings are referenced.

FIG. 8 is a block diagram of the entirety of a wireless video transmission system according to the second embodiment.

FIG. 9 illustrates an example of the screen displayed on a selection display unit.

FIG. 12 is a flowchart depicting the control process on video transmission performed by the control unit of a transmitter according to the second embodiment.

DESCRIPTION OF EMBODIMENTS

Figure 1:
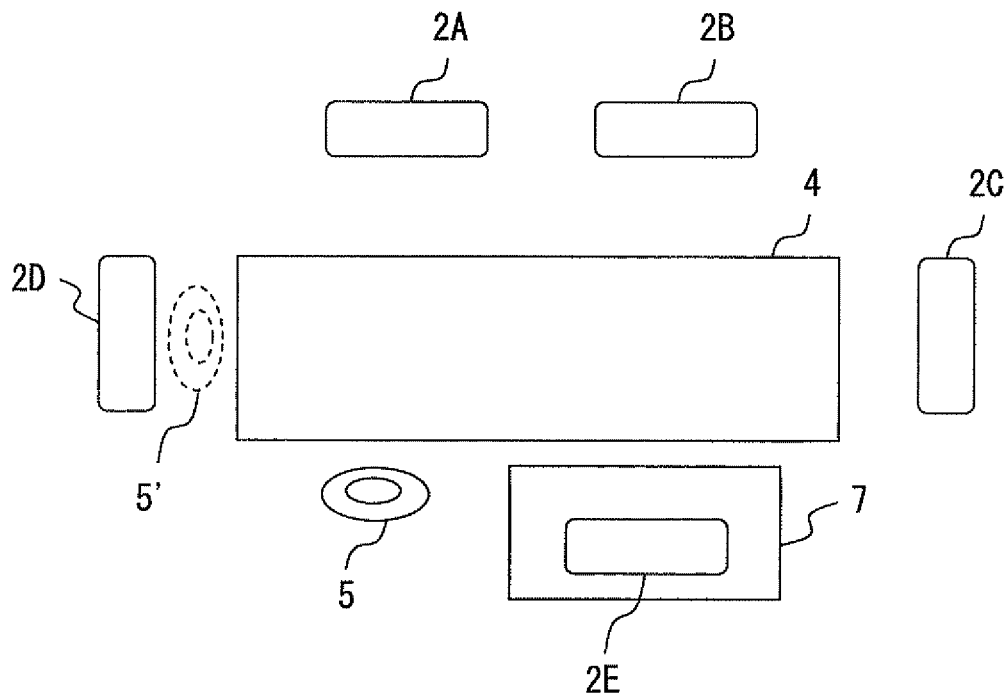
FIG. 1 illustrates an example of the configuration of an operating room provided with a wireless video transmission system.

FIG. 1 illustrates an example of the configuration of an operating room provided with a wireless video transmission system. Two or more ("five" in the example of FIG. 1) monitors 2A-2E are arranged around an operating table 4. A trolley 7 is provided with equipment required for endoscopic surgery such as an endoscope apparatus and a transmitter of a wireless video transmission system 10, which are not illustrated in FIG. 1.

The wireless video transmission system 10 uses a processor to perform image processing by performing image conversion on the endoscopic images or the like input from an endoscope (not Illustrated). The wireless video transmission system 10 transmits a video signal to one of the monitors 2A-2E via a transmitter 1 equipped with the trolley 7.

The monitors 2A-2E are arranged such that the displayed endoscopic image will be seen even if a position 5 of a practitioner is not at the position illustrated in FIG. 1. In other words, the monitors 2A-2E are arranged such that the displayed endoscopic image will be seen regardless of where the position 5 of a practitioner is around the operating table 4. For example, when a practitioner is at the position 5 as illustrated in FIG. 1, a "monitor 2A" is at the most convenient position for the practitioner to see. In this case, the wireless video transmission system 10 transmits a video signal to a receiver of the monitor 2A such that video will be displayed on the monitor 2A.

As described above, the wireless video transmission system 10 of FIG. 1 includes two or more monitors 2A-2E, and transmits a medical image by radio to a receiver that is connected to one of the monitors 2. A receiver that is connected to a monitor 2 at an appropriate position is set to a destination to which an image is transmitted according to a change or the like in the position 5 of a practitioner, and a medical image is transmitted by radio to a receiver of the set destination.

In FIG. 1, the configuration is illustrated in which five monitors 2A-2E are provided for the wireless video transmission system 10. However, in the following description, reference signs such as "A-E" will be given only when it is necessary to distinguish the monitors 2. The same applies to receivers 3 (the details will be described later) connected to the monitors 2, and to the configuration within the receiver 3.

Hereinafter, a method will be described in detail in which the wireless video transmission system 10 displays video on an appropriate monitor 2 from among the monitors 2 depending on the position 5 of a practitioner.

First Embodiment

Figure 2:
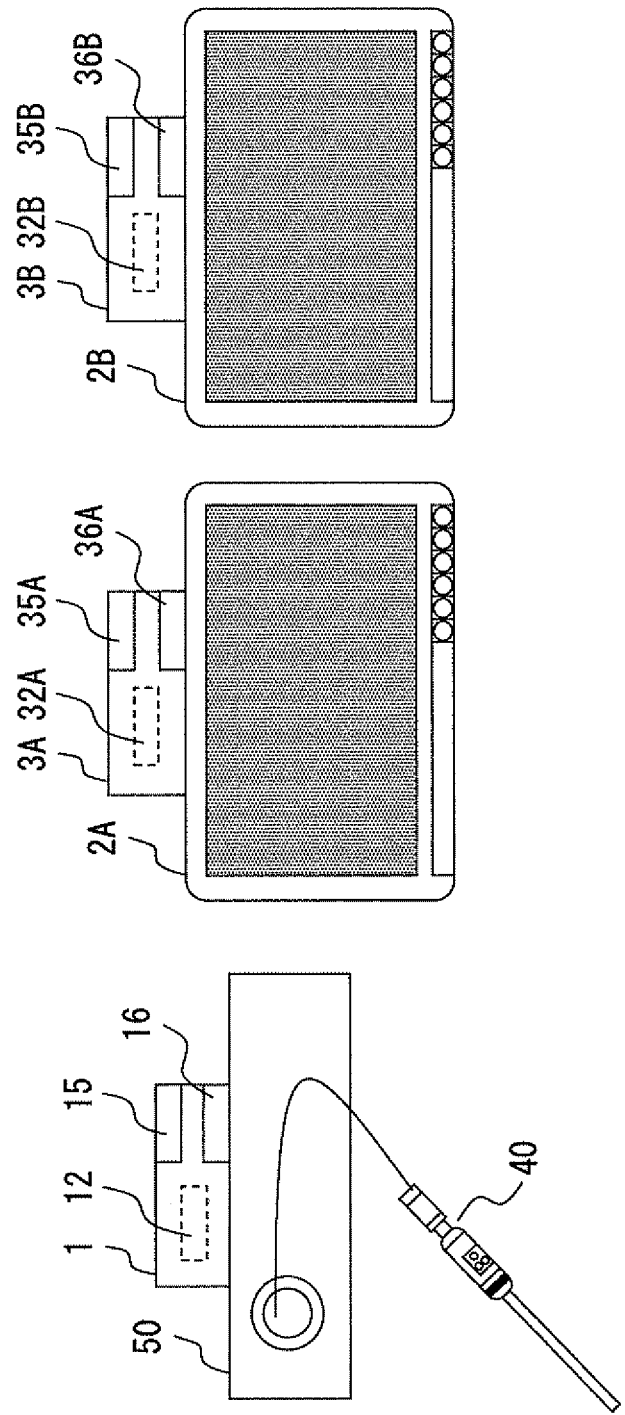
FIG. 2 is a block diagram of the entirety of a wireless video transmission system according to the first embodiment.

FIG. 2 is a block diagram of the entirety of a wireless video transmission system according to the present embodiment. Here, for the purposes of simplification, only the two monitors 2A and 2B of the monitors 2 are depicted. Note that none of the two monitors 2A and 2B of FIG. 2 is displaying video. A gray screen indicates that a monitor 2 is not displaying any video.

The transmitter 1 transmits the video of medical images or the like, which is acquired by an endoscope 40 and is image-processed by a processor 50, to the receiver 3 that is connected to the monitor 2 by radio. As described above, the wireless video transmission system 10 includes a plurality of monitors 2. Each of the monitors 2 is connected to the receivers 3, and of a plurality of receivers 3, the transmitter 1 transmits a video signal to one specified receiver 3. By doing this, video is displayed on a desired one of the monitors 2.

In the wireless video transmission system 10 according to the present embodiment, messages are exchanged between the transmitter 1 and the receiver 3 that is the destination to which a video signal is transmitted by radio through a channel at a specified frequency (hereinafter, referred to as a channel for short). The transmitter 1 acquires from the receiver 3 information used to distinguish the destination to which a video signal is to be transmitted by performing radio communication through a specified channel, and the transmitter 1 transmits a video signal by using the acquired information.

A selection operation unit 16 and a frequency channel display unit (CH display unit) 15 are arranged on the surface of the cabinet of the transmitter 1. The selection operation unit 16 accepts the channel selecting operation by an operator of the wireless video transmission system 10. The CH display unit 15 displays the channel that is selected by the selection operation unit 16.

A frequency channel operation unit (CH operation unit) 36 and a channel display unit (CH display unit) 35 are arranged on the surface of the cabinet of the receiver 3. The CH operation unit 36 is used to set a different channel to each of the monitors 2 (and the receivers 3 connected thereto) in the wireless video transmission system 10. The CH display unit 35 displays the channel set by the CH operation unit 36. The receiver 3 includes a memory 32. The memory 32 stores information to identify its own device.

In the example of FIG. 2, a channel "CH1" is assigned to the receiver 3A that is connected to the monitor 2A, and a channel "CH2" is assigned to the receiver 3B that is connected to the monitor 2B. When the transmitter 1 selects, for example, the channel "CH1", the transmitter is enabled to exchange messages with the receiver 3A. By doing this, the transmitter 1 acquires information to identify the receiver 3A.

The transmitter 1 includes a memory 12 to store in the memory 12 the information to identify the receiver 3, which is received from the receiver 3, and uses the stored information when transmitting a video signal. Hereinafter, the information to identify the receiver 3, which is used to transmit a video signal, will be referred to as an "individual identifier".

Figure 3:
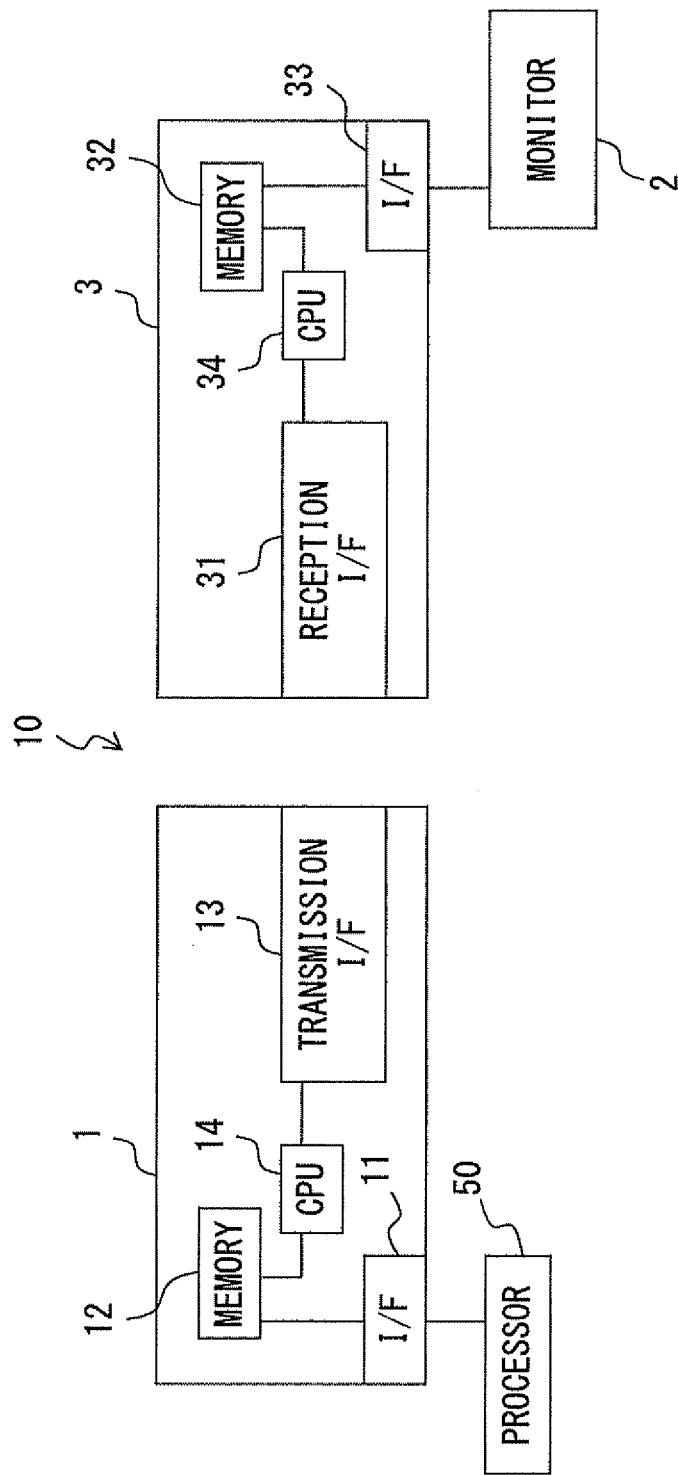
FIG. 3 is a block diagram of a transmitter and a receiver.

FIG. 3 is a block diagram of a transmitter and a receiver. In FIG. 3, only the configuration related to a method for transmitting a video signal according to the present embodiment is illustrated.

When a medical image is input from the processor 50, the transmitter 1 of FIG. 3 transmits the medical image by radio to the receiver 3 that is connected to the monitor 2.

The transmitter 1 includes an interface unit (I/F) 11, the memory 12, a transmission interface (hereinafter, referred to as transmission I/F) 13, and a CPU 14.

The interface unit (I/F) 11 is composed of, for example, a video connector, and the interface unit (I/F) 11 receives a video signal of a medical image or the like that is input from the processor 50, or a command or the like.

The memory 12 stores data or the like that is used by the transmitter 1 to perform various kinds of control or operation.

The transmission I/F 13 may perform radio communication with the receiver 3 that is connected to each of the monitors 2, and transmits a video signal of a medical image or the like that is input from the processor 50 to the receiver 3 by radio.

The CPU 14 performs control processing for the elements of the transmitter 1 such as control processing for the method for transmitting a video signal according to the present embodiment, or performs various kinds of operations.

The receiver 3 includes a reception interface (hereinafter, referred to as reception I/F) 31, a CPU 34, the memory 32, and an interface unit (I/F) 33.

The reception I/F 31 uses an individual identifier to receive a video signal of a medical image or the like transmitted from the transmission I/F 13 of the transmitter 1, by radio.

The interface unit (I/F) 33 is composed of, for example, a video connector, and the interface unit (I/F) 33 outputs a video signal received at the reception I/F 31 to the monitor 2.

The memory 32 stores data or the like that is used by the receiver 3 to perform various kinds of control or operation.

The CPU 34 performs control processing for the elements of the receiver 3 such as control processing for the display on the monitor 2 of the video signal received from the transmitter 1, or performs various kinds of operations.

As described above, the transmitter 1 transmits a video signal of a medical image to the receiver 3 of one of the monitors 2. The receiver 3 outputs the received video signal to the monitor 2. The monitor 2 displays the video input from the receiver 3. As the transmitter 1 sets the receiver 3 of an appropriate monitor 2 to the destination to which a video signal is to be transmitted, the video is displayed on the appropriate monitor 2 that corresponds to the position 5 of a practitioner (FIG. 1).

As described in the description of FIG. 2, the transmitter 1 of the wireless video transmission system 10 according to the present embodiment uses the channel selected by an operator via the selection operation unit 16 to exchange messages with a specified receiver 3. By doing this, the transmitter 1 acquires an individual identifier to be used for the transmission of a video signal. The configuration that is related to the process according to the present embodiment in which the transmitter 1 acquires an individual identifier from the receiver 3 will be described with reference to FIG. 4.

Figure 4:
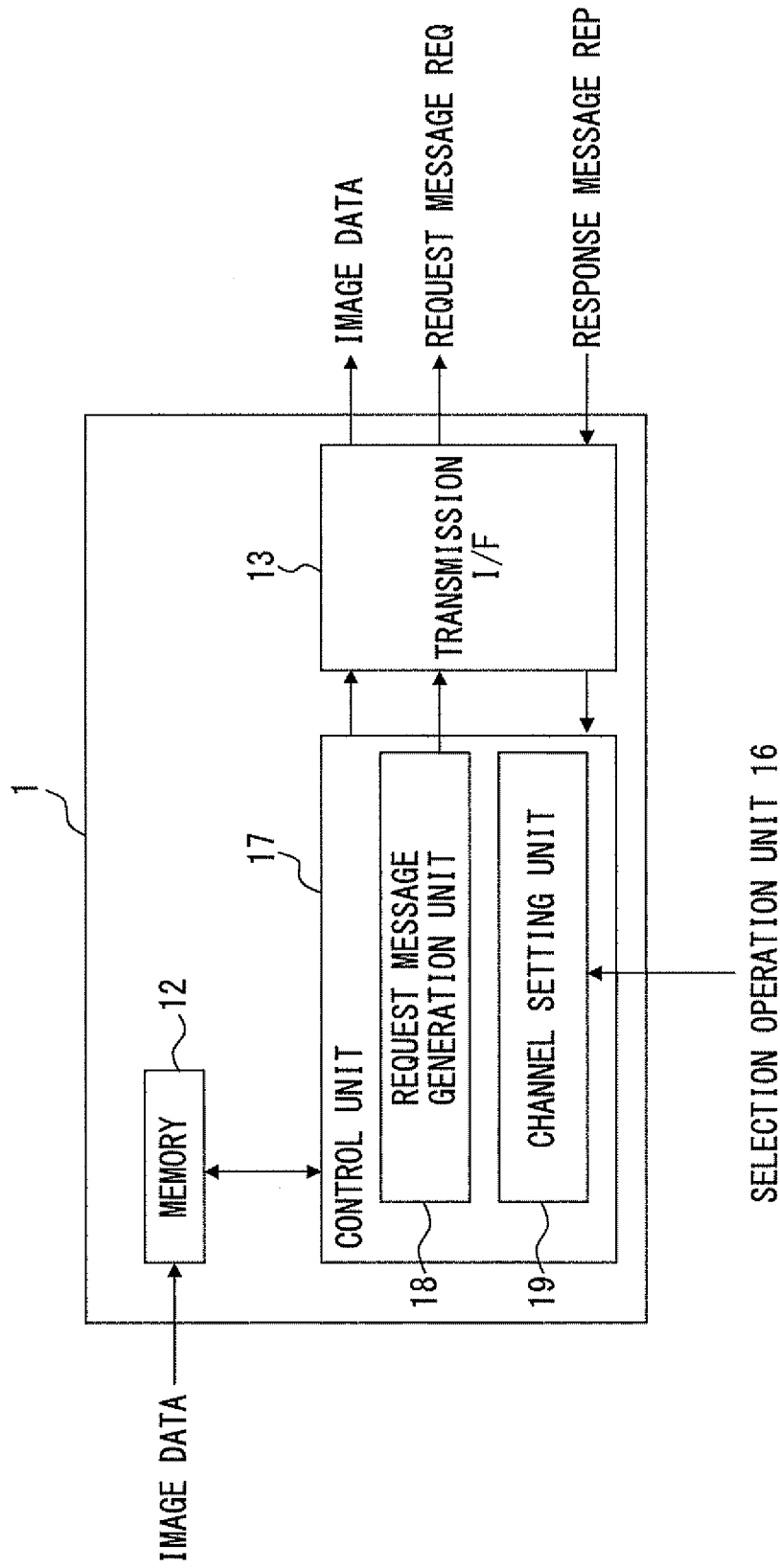
FIG. 4 is a functional block diagram of a transmitter according to the first embodiment.

FIG. 4 is a functional block diagram of the transmitter 1 according to the present embodiment. Here, the configuration related to a method for transmitting a video signal, and in particular, a method for acquiring an individual identifier from the receiver 3, will be mainly described. In the configuration of FIG. 4, the same reference signs will be assigned to elements that correspond to those of FIG. 3 or the like, and their description is omitted below.

A control unit 17 is included in the CPU 14 of FIG. 3, and the control unit 17 controls the elements in the transmitter 1 in relation to the process of transmitting a video signal to the receiver 3. The control unit 17 of the transmitter 1 according to the present embodiment includes, in particular, a request message generation unit 18 and a channel setting unit 19, and when the operation of selecting one monitor 2 that displays the video of medical images or the like from among the monitors 2 is received, the control unit 17 acquires an individual identifier for identifying the receiver 3 that is connected to the one selected monitor 2. Then, the control unit 17 controls the transmission I/F 13 such that the individual identifier will be used for the transmission of a medical image.

The channel setting unit 19 controls the channel that is selected via the selection operation unit 16 of FIG. 2 so as to be set as a channel used for exchanging messages. The request, message generation unit 18 generates a message to be transmitted to the receiver 3 in order to acquire an individual identifier. The control unit 17 gets the transmission I/F 13 transmit the message generated by the request message generation unit 18 by using the channel set by the channel setting unit 19. Then, the control unit 17 extracts an individual identifier from a response message to the transmitted message, and sets the individual identifier to the destination. By doing this, the control unit 17 controls the transmission of a video signal through the transmission I/F 13 of FIG. 3.

Figure 5:
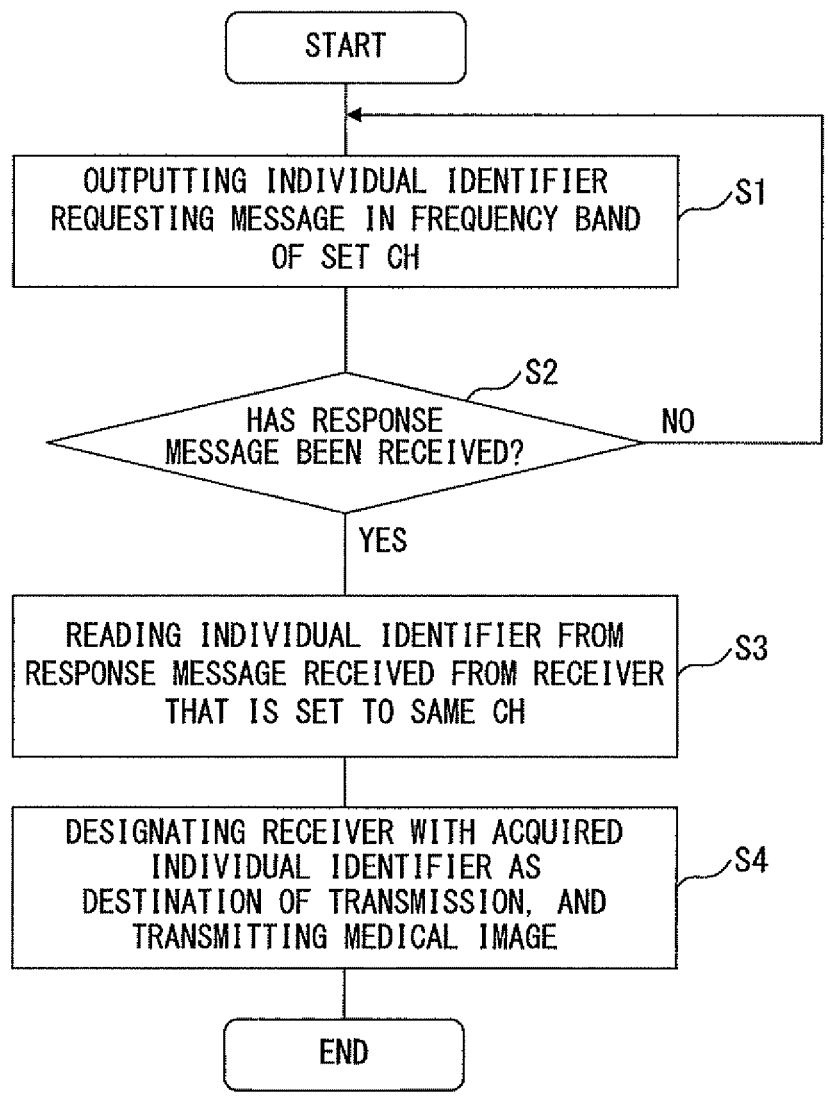
FIG. 5 is a flowchart depicting the control process on video transmission performed by the control unit of a transmitter according to the first embodiment.

FIG. 5 is a flowchart depicting the control process on the video transmission performed by the control unit 17 of the transmitter 1 according to the present embodiment. Once a channel is selected by the operation of the selection operation unit 16, the control unit 17 of the transmitter 1 starts the series of processes depicted in FIG. 5.

Firstly, in step S1, the control unit 17 controls the transmission I/F 13 to output a message requesting the acquisition of the individual identifier generated by the request message generation unit 18 in the frequency band of the channel set by the channel setting unit 19.

In step S2, the control unit 17 determines whether or not a response message has been received. When a response message is not received for a period that exceeds a specified period, the process returns to step S1 and a message is sent again. When a response message is received, the process shifts to step S3.

In step S3, the control unit 17 reads an individual identifier from a specified field in a response message received from (the reception I/F 31 of) the receiver 3 that is set to the same channel.

Finally, in step SA, the control unit 17 designates the reception I/F 31 of the receiver 3 that has the individual identifier acquired in step S3 as the destination of transmission, and transmits a video signal of a medical image or the like by radio. Then, the control unit 17 terminates the process.

Note that a known radio communication technique is used in the process of transmitting a video signal in step S4.

Figure 6:
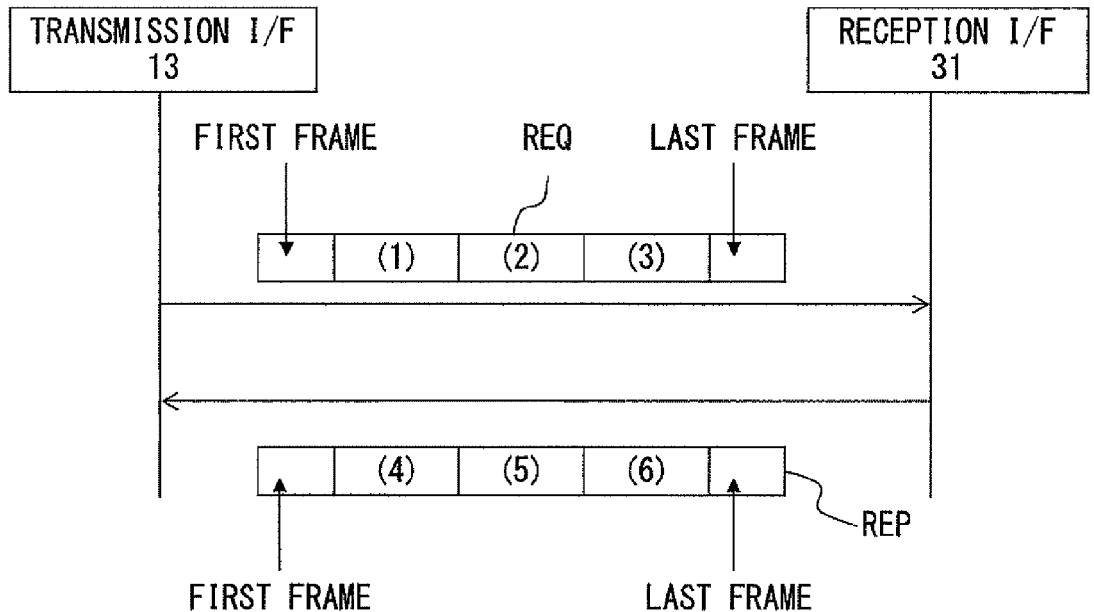
FIG. 6 illustrates an example of a sequence used when messages are exchanged between a transmitter and a receiver, and illustrates an example of the structure of messages that are exchanged between a transmitter and a receiver.

FIG. 6 illustrates an example of a sequence used when messages are exchanged between the transmitter 1 and the receiver 3, and illustrates an example of the structure of messages that are exchanged between the transmitter 1 and the receiver 3.

As illustrated in FIG. 6, a request message REQ that is transmitted from the transmission I/F 13 of the transmitter 1 includes (1) an individual identifier of the destination of transmission, (2) an individual identifier requesting command, and (3) an individual identifier of the transmission I/F 13.

When the transmitter 1 transmits a request, message REQ, "1" is set to field (1) as in, for example, a broadcast address, instead of the information of the reception I/F 31 of a specific receiver 3. Accordingly, a request message REQ is simultaneously transmitted to all the receivers 3 within the wireless video transmission system 10. However, only one of receivers 3 to which the same channel is set can receive the request message REQ.

When a request message REQ is received, the receiver 3 recognizes the received request message REQ as a request, from the transmitter 1 for an individual Identifier of its own device by referring to field (2), and generates a response message REP as illustrated in FIG. 6. The response message REP includes (4) an individual identifier of the transmission I/F 13, (5) an individual identifier response command, and (6) an individual identifier of the reception I/F 31.

Once a request message REQ is received, the receiver 3 assigns the individual identifier of the transmission I/F 13 retrieved from field (3) to field (4) in the response message REP, and assigns the individual identifier of the reception I/F 31 of its own device to field (6). Then, the receiver 3 transmits a generated response message REP.

When a response message REP is recognized by referring to field (5), the transmitter 1 retrieves an individual identifier of (the reception I/F 31 of) the receiver 3 from field (6), and stores the retrieved individual identifier in the memory 12. When a video signal is transmitted in step S4 of FIG. 5, an individual identifier read from the memory 12 is used.

Every time the selection operation unit 16 of FIG. 2 is operated and a channel is newly selected, the transmitter 1 exchanges messages by using the selected channel to acquire an individual identifier that indicates the destination to which the image data of a medical image or the like is to be transmitted, as illustrated in FIG. 6. When it is desired that the monitor 2 that is displaying video be switched to another monitor 2, an operator operates the selection operation unit 16 to switch the channel to the channel set to (the receiver 3 of) the monitor 2 on which it is desired that video be played.

Figure 7A:
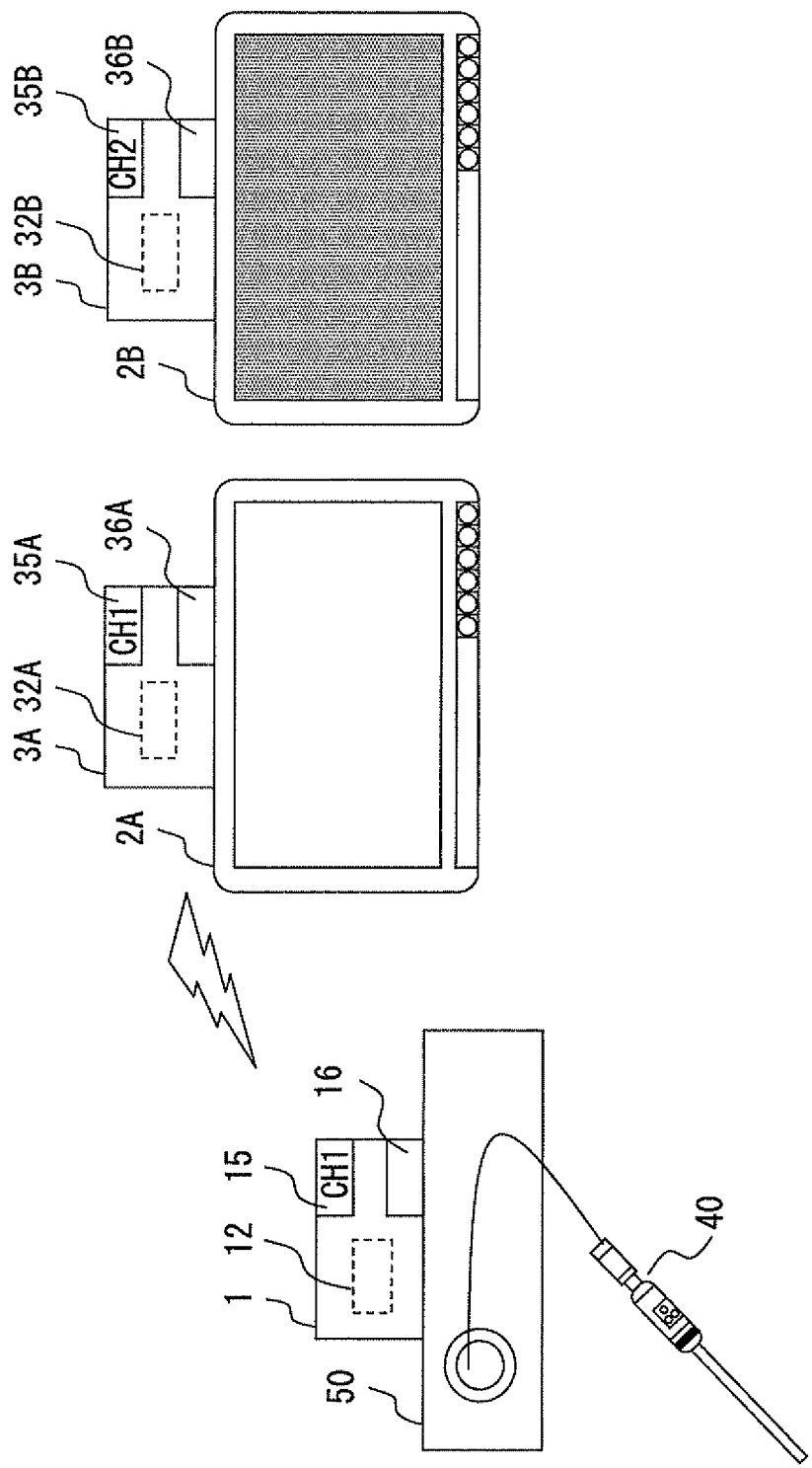
FIG. 7A illustrates the switching operation of monitors according to the operation of a selection operation unit (part 1).
Figure 7B:
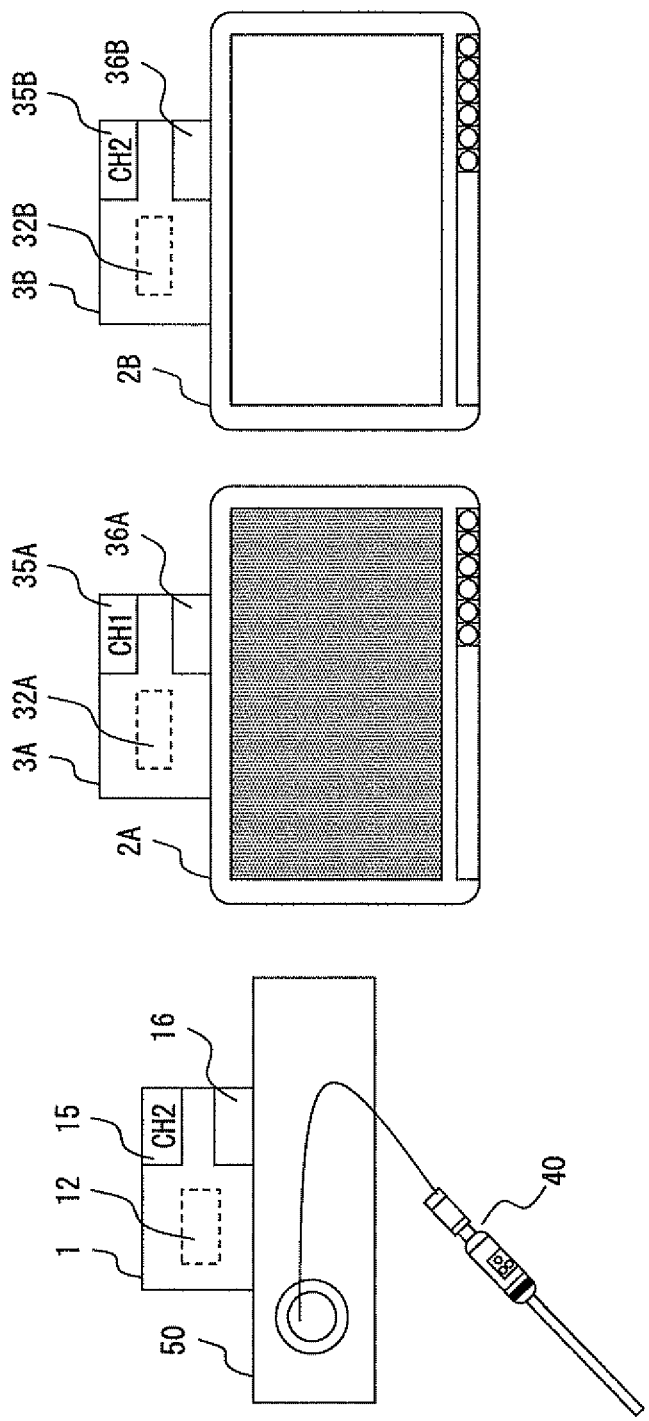
FIG. 7B illustrates the switching operation of monitors according to the operation of a selection operation unit (part 2).

FIG. 7A and FIG. 7B illustrate the switching operation of the monitors 2 according to the operation of the selection operation unit 16. FIG. 7A illustrates the case in which the channel used by the transmitter 1 for exchanging messages is set to "CH1". In this case, the transmitter 1 transmits the video signal of a medical image or the like by using the individual identifier acquired by exchanging messages with the receiver 3A to which channel "CH1" is set, and thus the video is displayed on the monitor 2A. The state in which video is being displayed is indicated as white on the screens in FIG. 7A and FIG. 7B. The other channel, i.e., the receiver 3B to which "CH2" is set in this example, is unable to communicate with the transmitter 1, and thus continues to be in a standby state. The monitor 2B indicates the state in which no video is being displayed (indicated as gray on the screen of the drawing).

When the practitioner moves around the operating table 4 and wants to switch the monitor 2 on which the video is to be displayed from the monitor 2A to the monitor 2B, the operator resets the channel of the transmitter 1 to "CH2". As the channel of the transmitter 1 is switched, the receiver 3 that communicates with the transmitter 1 is switched to the receiver 3B to which the channel CH2 is set, and the receiver 3 in a standby state is switched to the receiver 3A to which the channel CH1 is set.

When the channel is switched, the transmitter 1 transmits a message by using the newly set channel CH2. The transmitter 1 receives a response message that includes the individual identifier of the receiver 3B from the receiver 3B to which the channel CH2 is assigned, and sets the individual identifier acquired from the response message to the destination of transmission to transmit the video signal of a medical image or the like by radio. Accordingly, the receiver 3B that is connected to the monitor 2B receives a video signal, and the monitor 2 that is displaying video is switched from the monitor 2A to "monitor 2B".

A method for switching the monitor 2 on which video is displayed is described with reference to the two monitors 2A and 2B in the above, but even if three or more monitors 2 are provided for the wireless video transmission system 10, it is possible to perform switching by using a similar method to the above.

In other words, when five monitors 2A-2E are provided as in the example of the configuration of FIG. 1, five channels are arranged and set to monitors 2A-2E. The transmitter 1 is configured such that five channels are selectable. When the position 5 of a practitioner moves to a position 5' of FIG. 1, an operator operates the selection operation unit 16 of the transmitter 1 to switch the channel of the transmitter 1 to the channel being displayed on the CH display unit 35 of the monitor 2C that is at a convenient position for the practitioner to see from the destination to which the practitioner has moved. In a similar manner to the above, the transmitter 1 acquires the individual identifier of the receiver 3C that is connected to the desired monitor 2C by exchanging messages at the post-switched channel, and sets the newly acquired individual Identifier to the destination of transmission. Then, the transmitter 1 starts transmitting a video signal. By doing this, the monitor 2 on which the video is to be displayed is switched to the desired monitor 2C.

In FIG. 2 or the like, the transmitter 1 is illustrated as an external unit of the processor 50. However, the configuration of the transmitter 1 is not limited to this. For example, the transmitter 1 may be provided inside the processor 50, or may be provided, inside a camera head of the endoscope 40.

In a similar manner, the receiver 3 may be provided inside the monitor 2, or may be configured as an external unit, of the monitor 2.

As described above, according to the wireless video transmission system 10 of the present embodiment, it becomes possible to reduce the risk that, a practitioner or the like will trip over a video cable in an endoscopic surgery situation or the like by transmitting the video of medical images or the like by radio, and it also becomes possible to display the video on a desired one of the monitors 2.

An example of the configuration in which the selection operation unit 16 is arranged at the transmitter 1 that is mounted on the trolley 7 of FIG. 1 is described in the above, but the configuration of the selection operation unit 16 is not limited to such an example. For example, the selection operation unit 16 may be arranged at an operation unit of the endoscope 40 of FIG. 2. In such a configuration, the practitioner selects, by him/herself as an operator, the channel of the monitor 2 that is suitable for the display of the video of endoscope images or the like (i.e., the monitor 2C in the example of FIG. 1) at the position to which he/she moves (for example, the position 5' of FIG. 1) through the selection operation unit 16. The control unit 17 of the transmitter 1 that, has received a channel selecting operation at the selection operation unit 16 switches the channel of its own device to be used according to the received channel selecting operation. Then, the control unit 17 starts the series of processes of FIG. 5, and switches the monitor 2 on which video is displayed. If the selection operation unit 16 is arranged in a sterilized area, it becomes possible for a practitioner to perform operation by him/herself in a direct manner, and it becomes possible to switch between the monitors 2 in a more convenient manner.

Second Embodiment

In the first embodiment, a channel to be used between the transmitter 1 and the receiver 3 is designated through the selection operation unit 16 of the transmitter 1 and the transmitter 1 exchanges messages with the receiver 3 by using the designated channel and acquires a desired individual identifier. By contrast, in the present embodiment, the transmitter 1 acquires individual identifiers from all the receivers 3 arranged in the wireless video transmission system 10, and uses the acquired individual identifiers to perform communication with the receivers 3 in sequence. Then, a video signal is transmitted to the receiver 3 selected by the operator such that the video will be displayed on the monitor 2 that is connected to the destination receiver 3. The present embodiment is different from the first embodiment in the above respects.

Hereinafter, a video transmission method with the wireless video transmission system 10 according to the present embodiment will be described, where the main focus is on the differences from the first embodiment.

The configuration of the transmitter 1 and the receiver 3 is similar to that of FIG. 3, i.e., the configuration of the first embodiment. Thus, its description is omitted below. Also in the following description, the same reference signs will be assigned to elements similar to those in the first embodiment, and their description is omitted below.

FIG. 8 is a block diagram of the entirety of the wireless video transmission system 10 according to the present embodiment.

The transmitter 1 and a plurality of receivers 3 set a specified common channel to the channel to be used, and exchange messages by using the set channel. When a request message REQ is received, the receiver 3 reads an individual identifier stored in the memory 32 of its own device, and transmits a response message REP in which the read individual identifier is included. The transmitter 1 acquires individual identifiers from all the receivers 3 in the wireless video transmission system 10, and stores the acquired individual identifiers in the memory 12.

The transmitter 1 reads the individual identifiers stored in the memory 12 that identify all the receivers 3 on a one-by-one basis, and then starts performing communication. FIG. 8 illustrates the case in which communication is being performed with the receiver 3A connected to the monitor 2A by using the individual identifier of the receiver 3A.

The monitor 2 has a selection display unit 70 on its screen that lets an operator choose whether or not to display video on the monitor 2. In the example of FIG. 8, the transmitter 1 is performing communication by using the individual identifier of the receiver 3A, and an operator chooses whether or not to display the video on the monitor 2A through the selection display unit 70 on the monitor 2A connected to the receiver 3A. The selection of whether not to display the video on the monitor 2A is input to the transmitter 1 through a selection operation unit 41 arranged at an operation unit 45 or the like of the endoscope 40.

Figure 10:
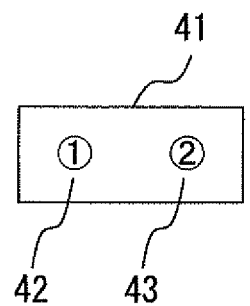
FIG. 10 illustrates an example of a selection operation unit.

FIG. 9 illustrates an example of the screen displayed on the selection display unit 70, and FIG. 10 illustrates an example of the selection operation unit 41.

As illustrated in FIG. 9, the selection display unit 70 of the monitor 2 displays a message 71 that lets an operator choose whether or not to display video on the monitor 2. Two buttons (button 1 and button 2) 42 and 43 are arranged on the selection operation unit 41 of FIG. 10. In the example of FIGS. 9 and 10, an operator presses a button 42 according to what is indicated by the message 71 when it is desired that video be displayed on the monitor 2 that is displaying the message 71, and the operator presses a button 43 when it is desired that the video be displayed on another one of the monitors 2.

When the monitor 2 on which, the video is to be displayed is selected through the selection operation unit 41 (when the button 42 is pressed in the example of FIG. 10), from that time on, the transmitter 1 transmits the video of medical images or the like by radio to the receiver 3 that is connected to the selected monitor 2.

Figure 11:
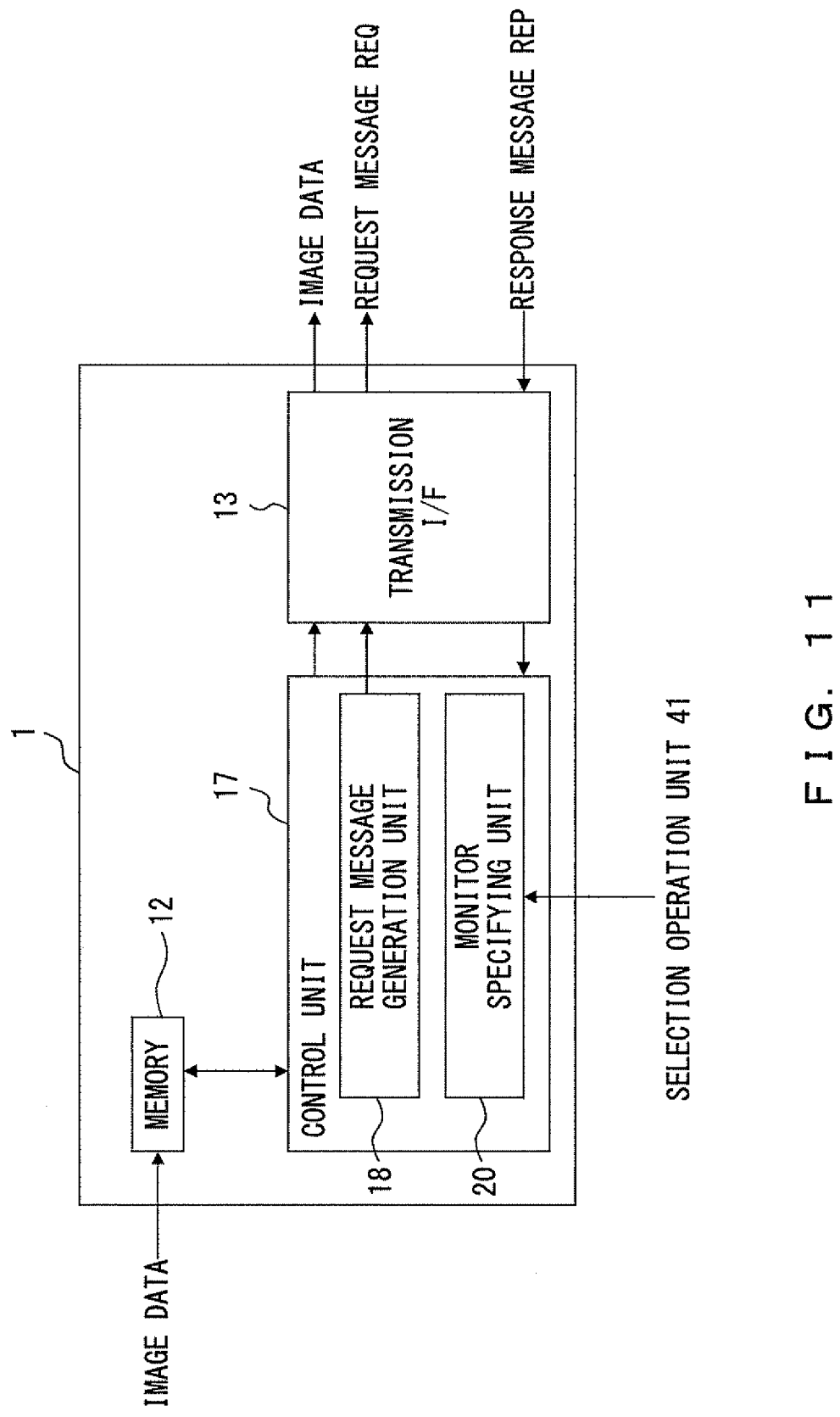
FIG. 11 is a functional block diagram of a transmitter according to the second embodiment.

FIG. 11 is a functional block diagram of the transmitter 1 according to the present embodiment. The control unit 17 of the transmitter 1 illustrated in FIG. 11 includes the request message generation unit 18 and a monitor specifying unit 20.

The monitor specifying unit 20 receives the information input by an operator through the selection operation unit 41, which indicates whether or not the video is to be displayed on the monitor 2 that is displaying the selection display unit 70 of FIG. 8, and the monitor specifying unit 20 passes the received information to the control unit 17. The control unit 17 refers to the information received from the monitor specifying unit 20 to determine whether or not to display the video on the monitor 2 that is displaying the selection display unit 70. When it is determined that the video is to be displayed on the monitor 2 that is displaying the message 71 on the selection display unit 70, the control unit 17 controls the transmission I/F 13 so as to start transmitting a video signal to the receiver 3 that is connected to the selected monitor 2.

FIG. 12 is a flowchart depicting the control process on the video transmission performed by the control unit 17 of the transmitter 1 according to the present embodiment.

Firstly, when the control unit 17 detects in step S11 that either one of the buttons 42 and 43 of the selection operation unit 41 of FIG. 10 has been pressed, the control unit 17 transmits a request message REQ that requests an individual identifier in step S12.

In step S13, the control unit 17 receives response messages REP from the reception I/Fs 31 of the receivers 3, and extracts individual identifiers from a specified field in the response message REP (for example, field (6) in FIG. 6). Then, the control unit 17 stores the extracted identifiers in the memory 12 in the order of acquisition. When the response messages REP have been received from all the receivers 3 and the individual identifiers that identify the receivers 3 have been stored in the memory 12, the process shifts to step) S14.

In step S14, the control unit 17 reads the firstly stored individual identifier from among the individual identifiers stored in the memory 12. Then, the control unit 17 controls the transmission I/F 13 so as to start communication with the reception I/F 31 of the receiver 3 that has the read individual identifier.

Note that a method for exchanging messages between the transmitter 1 and the receiver 3 in step S13 and step S14 as well as the format or the like of messages are as illustrated in FIG. 6 and are similar to those in the first embodiment.

In step S15, the control unit 17 determines whether or not the information input from the selection operation unit 41 is the information indicating that the video is to be displayed on the monitor 2 connected to the receiver 3 that is performing communication. When the input information is the information indicating that the video is to be displayed on the monitor 2 connected to the receiver 3 that is performing communication, the process shifts to step S20. When the input information is the information indicating that the video is not to be displayed on the monitor 2 connected to the receiver 3 that is performing communication, the process shifts to step S16.

In step S16, the control unit 17 reads the secondly stored individual identifier from among the individual identifiers stored in the memory 12. Then, the control unit 17 controls the transmission I/F 13 so as to start communication with the reception I/F 31 of the receiver 3 that has the read individual identifier, in a similar manner to the process in step S14.

From that time on, similar processes are performed in sequence (see steps S17 to S19 in FIG. 12), and when the information indicating that the video is to be displayed on the monitor 2 whose transmitter 1 is connected to the receiver 3 that is performing communication is input through the selection operation unit 41, the process shifts to step S20.

In step S20, the control unit 17 transmits the video signal of a medical image or the like to the receiver 3 that is connected to the monitor 2 selected by the selection operation unit 41, and terminates the process.

In the system configuration of FIG. 1, a case will be described in which, for example, the monitor 2A is switched to the monitor 2C from among five monitors 2 when a practitioner has moved from the position 5 to the position 5'. In this case, firstly, the selection operation unit 41 is pressed and messages are exchanged between the transmitter 1 and the receivers 3A-3E, and individual identifiers are acquired from all the receivers 3A-3E. The acquired individual identifiers are stored in the memory 12, and communication starts in sequence. The receiver 3 that has started communicating with the transmitter 1 reads the message 71 from the memory 32 of its own device, and displays the message 71 on the selection display unit 70 of the connected monitor 2. The operator is able to switch the monitor 2 on which video is displayed to a desired monitor 2 (i.e., the monitor 2C in this case) by pressing the button 42 of FIG. 10 when the message 71 is displayed on the monitor 2C.

As described above, according to the wireless video transmission system 10 according to the present embodiment, in a similar manner to the embodiment described above, it becomes possible to transmit the video of medical images or the like by radio, and to display video on a desired monitor 2 of the monitors 2.

Furthermore, the wireless video transmission system 10 according to the present embodiment has an advantage that only one frequency channel is required to acquire individual identifiers. When the selection operation unit 41 is arranged at the operation unit 45 or the like of the endoscope 40, it becomes possible for a practitioner to operate the selection operation unit 41 to select a desired one of the monitors 2 by him/herself, and to display the video of endoscope images or the like on the selected monitor 2.

Third Embodiment

In the first and second embodiments, the transmitter 1 acquires an individual identifier to be used for identifying the receiver 3 by exchanging messages between the transmitter 1 and the receiver 3, and the transmitter 1 transmits video by using the acquired individual identifier. By contrast, the transmitter 1 holds individual identifiers for all the receivers 3 included in the wireless video transmission system 10 in the present embodiment, which is different from the first and second embodiments.

Hereinafter, a video transmission method with the wireless video transmission system 10 according to the present embodiment will be described, where the main focus is on the differences from the embodiments described above. The configuration of the transmitter 1 and the receiver 3 is similar to that of FIG. 3, and thus its description is omitted below. Also in the following description, the same reference signs will be assigned to elements similar to those in the first or second embodiment, and their description is omitted below.

Figure 13:
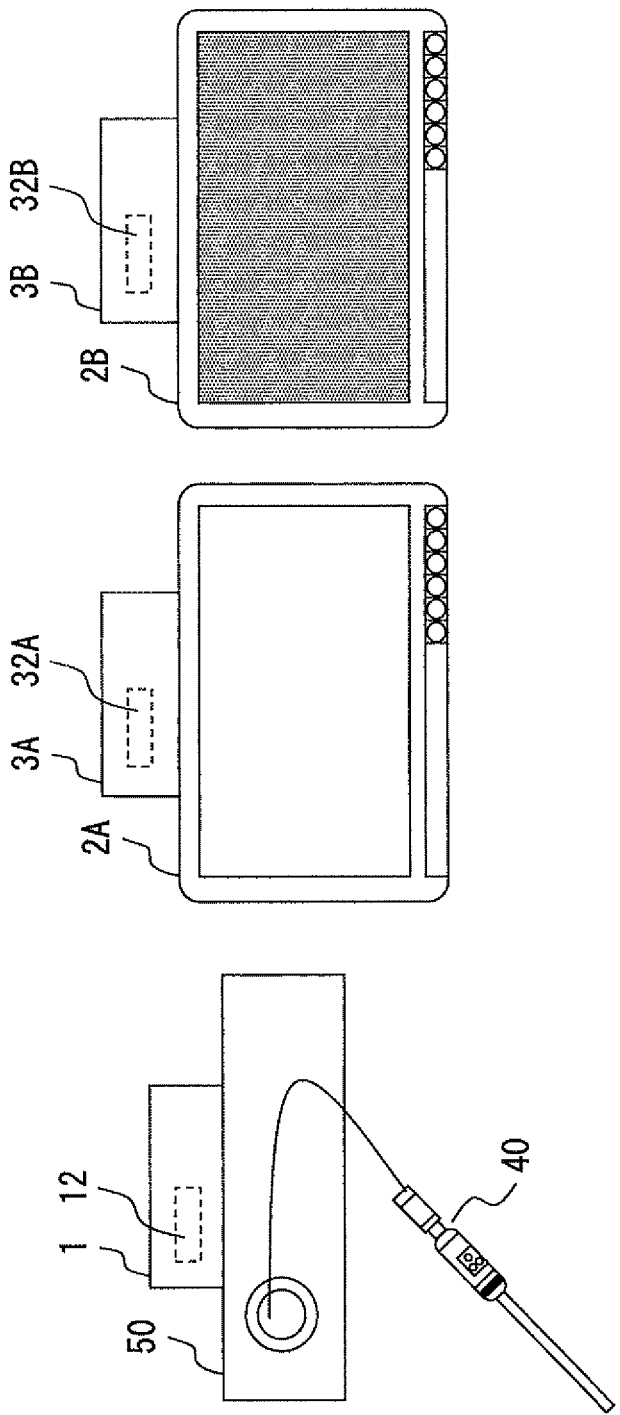
FIG. 13 is a block diagram of the entirety of a wireless video transmission system according to the third embodiment.

FIG. 13 is a block diagram of the entirety of the wireless video transmission system 10 according to the present embodiment.

The transmitter 1 stores the individual identifiers of all the receivers 3 of the system in the memory 12. In the memory 12, it is possible to store individual identifiers so as to be associated with the receivers 3. In the present embodiment, the individual identifier of the receiver 3A is stored in the first line of the table, structure, and the individual identifier of the receiver 3B is stored in the second line of the table structure. Each of the receivers 3 stores the individual identifier of its own device in the memory 32.

Here, it is assumed it is desired that video be displayed on the monitor 2A from among the two monitors 2A and 2B illustrated in FIG. 13. In this case, when an operator inputs, for example, the information indicating the monitor 2 on which it is desired that the video be displayed through the selection operation unit 41 of FIG. 10, the transmitter 1 reads from the memory 12 the individual identifier of the receiver 3 that corresponds to the monitor 2 indicated by the input information. Then, the transmitter 1 sets the read individual identifier to the destination of transmission, and transmits a video signal thereto.

Figure 14:
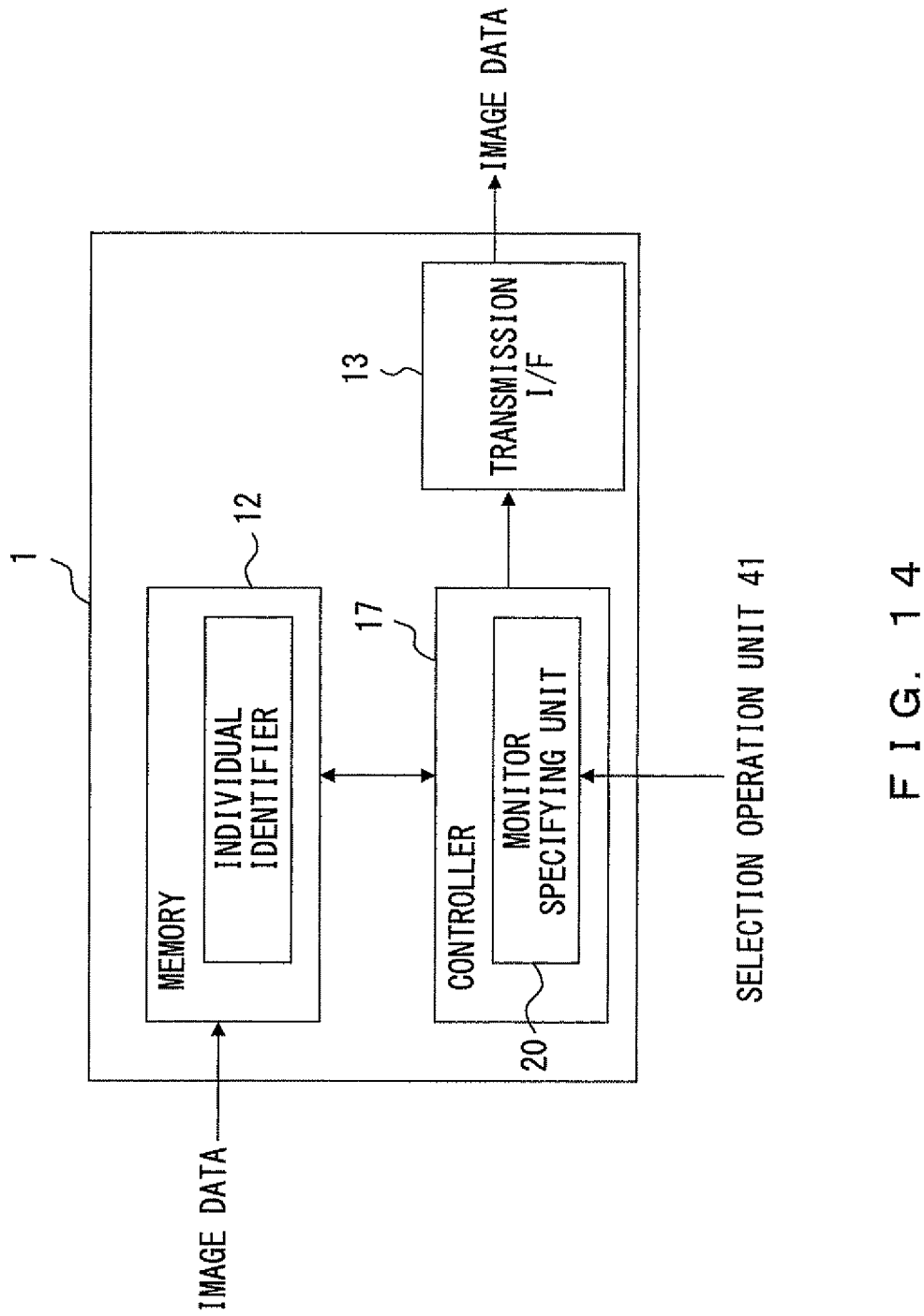
FIG. 14 is a functional block diagram of a transmitter according to the third embodiment.

FIG. 14 is a functional block diagram of the transmitter 1 according to the present embodiment. The control unit 17 of the transmitter 1 illustrated in FIG. 14 includes the monitor specifying unit 20.

The monitor specifying unit 20 receives the information indicating the monitor 2 on which the video is to be displayed from among the monitors 2 in the wireless video transmission system 10, which is input by the operator through the selection operation unit 41 of FIG. 10.

As in the case in which the number of the monitors 2 is two is described as an example in FIG. 13, it is sufficient for the selection operation unit 41 to assign each monitor to one of the two buttons as illustrated in FIG. 10, where, for example, the monitor 2A and the monitor 2B are assigned to the button 42 and the other button 43. When the operator presses the button that corresponds to the monitor 2 on which it is desired that the video to be displayed from among the two buttons, it becomes possible to determine which of the monitors 2 is selected.

Figure 15:
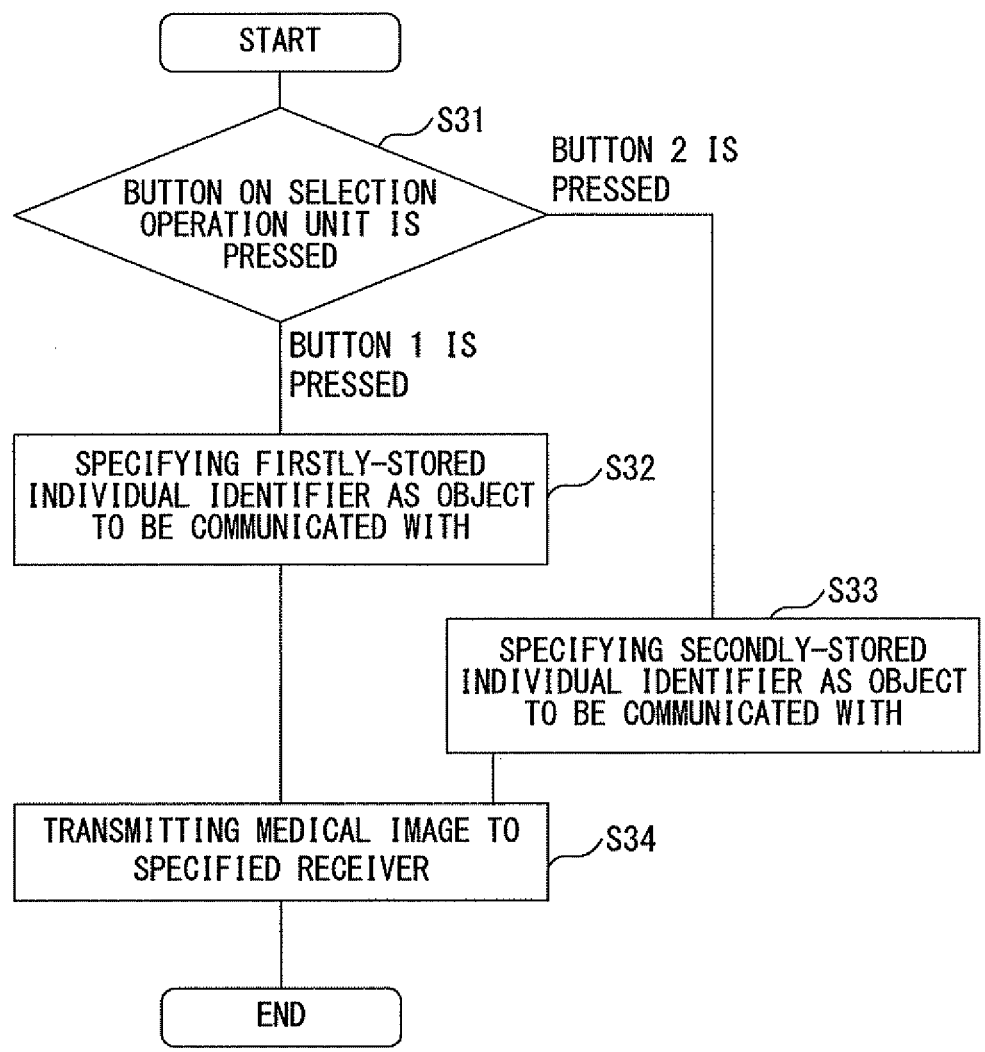
FIG. 15 is a flowchart depicting the control process on video transmission performed by the control unit of a transmitter according to the third embodiment.

FIG. 15 is a flowchart depicting the control process on the video transmission performed by the control unit 17 of the transmitter 1 according to the present embodiment. The case in which the number of the monitors 2 is two and the configuration of the selection operation unit 41 is as illustrated in FIG. 10 will be described as an example.

Firstly, in step S31, the control unit 17 detects that a button on the selection operation unit 41 is pressed. When the pressed button is the button 42 of FIG. 10, the process shifts to step S32. When the pressed button is the button 43 of FIG. 10, the process shifts to step S33.

In step S32, the control unit 17 specifies the firstly stored individual identifier as an object, to be communicated with from among the individual identifiers stored in the memory 12. Then, in step S34, the control unit 17 sets the individual identifier specified as the object to be communicated with to the destination of transmission, and transmits a video signal to the reception I/F 31 of the receiver 3. After that, the process is terminated.

In step S33, the control unit 17 specifies the secondly stored individual identifier as an object, to be communicated with from among the individual identifiers stored in the memory 12. In step S34, the control unit 17 performs a process similar to the above, and terminates the process.

A method for switching the monitors 2 where two monitors 2A and 2B are used as an example is described in the above, but it is still possible to perform switching with a similar method even if three or more monitors 2 are arranged in the wireless video transmission system 10.

For example, it is assumed that a practitioner has moved from the position 5 to the position 5' in an example of the configuration where five monitors 2A-2E are arranged as illustrated in FIG. 1. As a method for switching the monitors 2, for example, the selection operation unit 41 may be provided with the same number of buttons as the number of the monitors 2. In this case, when an operator presses the button that is assigned to the monitor 2C at the position corresponding to the position 5' to which the practitioner has moved, the transmitter 1 sets the individual identifier of the receiver 3C to the destination of transmission, and sends a video signal thereto. Alternatively, the selection operation unit 41 is provided with two buttons as illustrated in FIG. 10, and it may be configured such that the buttons indicate whether or not to display video on a particular monitor 2. In this case, an operator is asked to indicate whether or not to display video on each of the five monitors 2A-2E. The operator presses a specified button to instruct the monitor 2C to display video. By doing this, the transmitter 1 sets the individual identifier of the receiver 3C to the destination of transmission, and sends a video signal thereto, in a similar manner to the above.

As described above, according to the wireless video transmission system 10 of the present embodiment, in a similar manner to the embodiments described above, it becomes possible to transmit the video of medical images or the like by radio, and to display the video on a desired one of the monitors 2.

In the present embodiment, the transmitter 1 holds in advance the individual identifiers of the receivers 3 that are connected to all the monitors 2 arranged in the wireless video transmission system 10, and thus it is not necessary to exchange messages to acquire an individual identifier.

Furthermore, when the selection operation unit 41 is arranged at the operation unit 45 or the like of the endoscope 40, it becomes possible for a practitioner to operate the selection operation unit 41 to select a desired one of the monitors 2 by him/herself, and to display the video of endoscope images or the like on the selected monitor 2.

Apart from the above, various applications and modifications of the present invention are possible without departing from the spirit or scope of the invention. For example, some elements may be deleted from the overall configuration of the embodiments described above, or some elements of different embodiments may be combined as necessary.

According to the present invention, it becomes possible to reduce the risk that a practitioner or the like will trip over a video cable, and it also becomes possible to display the medical image of an endoscopic image or the like on a desired monitor from among two or more monitors.

What is claimed is:

1. A transmission device used in a wireless video transmission system in which a medical image is transmitted and received by radio communication, the transmission device comprising:
a transmission unit capable of performing radio communication with a plurality of receiving devices which are respectively connected to a plurality of display apparatuses and which receive the medical image to be displayed on the display apparatuses;
a control unit configured to acquire an identifier for identifying a receiving device connected to a selected single display apparatus when an instruction is received to select one display apparatus on which the medical image is to be displayed from among the display apparatuses, and configured to control the transmission unit such that the identifier will be used when the medical image is transmitted; and
a generating unit configured to generate an acquisition request requesting identifiers of the receiving devices connected to the display apparatuses respectively, wherein
the control unit controls the transmission unit to transmit the acquisition request by using a specified channel set to the receiving devices in common, and controls the transmission unit such that an identifier indicating the receiving device connected to the selected display apparatus from among identifiers included in responses given to the acquisition request will be set to a destination of transmission and the medical image will be transmitted, and
in a control process for the transmission unit, the control unit
acquires a first identifier from a firstly received first response from among the responses received from the receiving devices connected to the display apparatuses, and sets the first identifier to a destination of transmission and controls the transmission unit so as to start performing radio communication with a first receiving device connected to a first display apparatus,
controls the transmission unit so as to start transmitting the medical image to the first receiving device when an instruction is received to select the first display apparatus, and acquires a second identifier from a second response received after the first response and sets the second identifier to the destination of transmission to control the transmission unit so as to start performing the radio communication with a second receiving device when an instruction is received not to select the first display apparatus, and
repeats, until an instruction to select the receiving device that is performing the radio communication is received, the above processes which comprise:
starting performing radio communication with one receiving device connected to one display apparatus by use of one identifier; and
according to whether or not an instruction has been received to select the display apparatus to which the receiving device that is performing communication is connected, starting transmitting the medical image or further starting performing radio communication with another receiving device connected to another display apparatus by use of another identifier.

2. A wireless video transmission system, comprising:
the transmission device according to claim 1; and
the plurality of receiving devices, each of the receiving devices comprising a receiver configured to receive the medical image transmitted from the transmission unit.

3. A wireless video transmission system comprising:
the transmission device according to claim 1, comprising:
a video signal transmission unit for transmitting a video signal by radio, which is used to display an observation image;
an identification signal transmission unit for selectively transmitting a first identification signal and a second identification signal by radio, which are used to specify a monitor on which the video signal is to be displayed;
a first monitor comprising:
a first identification signal recognition unit configured to recognize the first identification signal transmitted from the transmission device;

a first video signal receiving unit configured to receive the video signal from the transmission device according to a result of recognition by the first identification signal recognition unit;

a first display unit capable of displaying the video signal received by the first video signal receiving unit; and a second monitor comprising:

a second identification signal recognition unit configured to recognize the second identification signal transmitted from the transmission device;

a second video signal receiving unit configured to receive the video signal from the transmission device according to a result of recognition by the second identification signal recognition unit;

a second display unit capable of displaying the video signal received by the second video signal receiving unit;

wherein:

the transmission device controls the identification signal transmission unit to transmit the acquisition request by using a specified channel set to the first and second monitors in common, and controls the video signal transmission unit such that an identifier indicating the selected receiving unit of the first or second monitor from among the identifiers included in the responses given to the acquisition request will be set to the destination of transmission and the medical image will be transmitted, and in the control process, the transmission device:

acquires the first identifier from among the responses received from the first and second monitors, and controls the video signal transmission unit so as to start performing the radio communication with the first or second monitor, controls the video signal transmission unit so as to start transmitting the medical image to the first or second monitor that is performing the radio communication when an instruction is received to select the first or second monitor that is performing the radio communication, and acquires the second identifier and sets the second identifier to the destination of transmission to control the video signal transmission unit so as to start performing the radio communication with the first or second monitor when an instruction is received not to select the first or second monitor that is performing communication, and repeats the above processes until an instruction to select the first or second monitor that is performing communication is received.

4. A transmission device used in a wireless video transmission system in which a medical image is transmitted and received by radio communication, the transmission device comprising:

a transmission unit configured to perform radio communication with a plurality of receiving devices which are each connected to a corresponding one of a plurality of display apparatuses and which are configured to receive the medical image from the transmission unit;

a generating unit configured to generate an acquisition request requesting identifiers of the receiving devices; and a control unit configured to control the transmission unit such that an identifier of a receiving device connected to a selected display apparatus will be used when the medical image is transmitted, wherein the control unit:

controls the transmission unit to transmit the acquisition request by using a specified channel set to the receiving devices in common, and beginning with a firstly received response given to the acquisition request and continuing in an order that responses given to the acquisition request are received from the receiving devices, acquires a corresponding identifier from the response received from the receiving device, sets the corresponding identifier to a destination of transmission, and controls the transmission unit so as to start performing radio communication with the receiving device from which the response was received, and when an instruction is received to select the display apparatus to which the receiving device that is performing the radio communication is connected, controls the transmission unit so as to start transmitting the medical image to the receiving device that is performing the radio communication.

5. The transmission device according to claim 4, further comprising:

a storage unit configured to store the identifiers included in the responses given to the acquisition request, wherein the control unit acquires the corresponding identifier by reading the corresponding identifier from the storage unit.

6. A wireless video transmission system, comprising:

the transmission device according to claim 4; and the plurality of receiving devices, each of the receiving devices comprising a receiver configured to receive the medical image transmitted from the transmission unit.

* * * * *